Sept. 28, 1943. R. L. BYRUM Plant Pat. 601
ROSE PLANT
Filed March 29, 1943
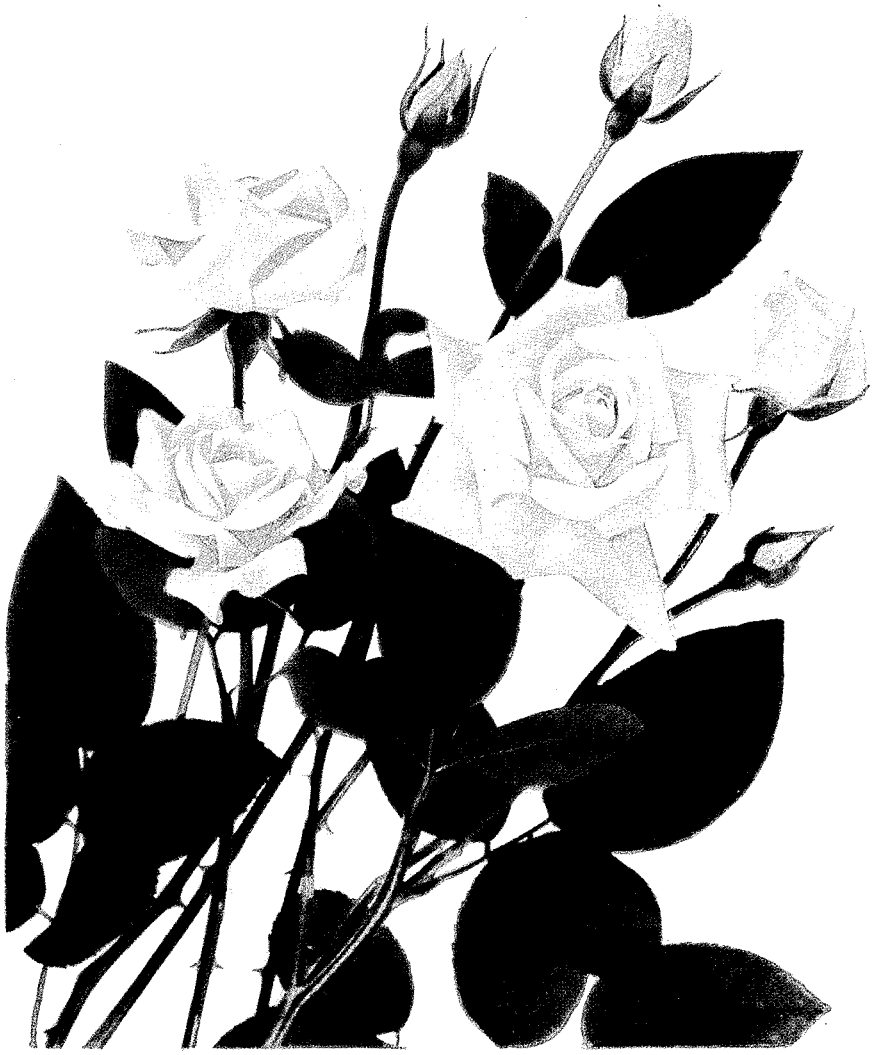
Inventor
Roy L. Byrum
By Robbins & Robbins
Attorneys Patented Sept. 28, 1943

Plant Pat. 601

UNITED STATES PATENT OFFICE

601

ROSE PLANT

Roy L. Byrum, Richmond, Ind., assignor to Joseph H. Hill Company, Richmond, Ind., a corporation of Indiana Application March 29, 1943, Serial No. 481,003

1 Claim. (Cl. 47—61)

The present invention relates to a new and distinct variety of hybrid polyantha rose plant, originating as a cross between two known varieties "Juanita" and "Mrs. R. M. Finch."

The new variety as thus produced, and hereinafter more particularly described, constitutes a marked improvement over its parents in a number of important respects, among which may be noted that while the flowers are similar to those of the pollen parent, they are larger and darker in color; its growth is very vigorous and resembles the seed parent in this characteristic; it is more productive than "Mrs. R. M. Finch," since the latter is known to slow down in cut flower production in the winter season; its flowers, furthermore, are larger than those of "Juanita" and they have many more petals than "Juanita." Again, it differs from "Mrs. R. M. Finch" in that the stems are longer and more suitable for cut flowers, the foliage is larger, and semi-glossy; more thorny with thorns not so long or hooked so much. Insofar as fragrance is concerned, it is similar to "Mrs. R. M. Finch."

It will thus be seen that this new variety possesses many advantages over its parents, and also others considered either from the standpoint of individual or combined characteristics insofar as the particular class of roses to which it relates is concerned.

Asexual reproduction shows that these characteristics hold true through succeeding propagations, by cuttings, grafting, and budding.

The following is a detailed description of this new variety, color terminology being in accord with Ridgway's Color Standard and with general dictionary terms:

Type: Half hardy; bush; greenhouse; outdoor; seedling; for cut flowers and garden decoration.
Class: Hybrid polyantha.
Breeding or discovery: Seedling.
*Pollen parent.*—"Mrs. R. M. Finch."
*Seed parent.*—"Juanita."

*Flower*

Locality where grown: Richmond, Indiana.
Flowers borne: Singly, two and three to stem; in irregular cluster; on strong, medium length stems.
Quantity of bloom: Abundant; outdoors and in greenhouse.
Continuity: Continuous in greenhouse.
Fragrance: Nutty.
Bud:
*Peduncle.*—Medium length; medium heavy; erect; stiff; light yellowish green; entirely smooth; numerous yellow hairs and prickles.
*Before calyx breaks.*—*Size*—small. *Form*—short, pointed, with a conspicuous neck; foliaceous appendages on the surface of the bud; with stout, much cut, bristle-like foliaceous parts extending beyond the tip of the bud equal to three-fourths or more of its length.
*As calyx breaks.*—*Color*—Begonia Rose, Plate I.
*As first petal opens.*—*Size*—small. *Form*—short; flat; ovoid. *Color*—outside—Spinel Pink, Plate XXVI; inside—Thulite Pink, Plate XXVI. *Opening*—opens up well.
Bloom:
*Size.*—When fully open, small, 1½ inches to 2 inches.
*Petalage.*—Double; from 50 to 60 petals arranged irregularly.
*Form.*—Flat; full; petals remaining at first very tightly rolled outward; becoming later, at maturity, very loosely rolled outward.
Petals: Thick; soft; inside, shiny; outside, satiny.
*Shape.*—*Outside*—obovate. *Intermediate*—obovate. *Inside*—obovate; scalloped, irregular, with one notch.

This description of a newly opened flower was made from a rose grown in a greenhouse in August, 1942, at Richmond, Indiana:

*Color.*—*Outside petal*—outside surface—Thulite Pink, Plate XXVI; inside surface—Cameo Pink, Plate XXVI, pencilled with Thulite Pink, Plate XXVI. *Intermediate petal*—outside surface—Thulite Pink, Plate XXVI; inside surface—Cameo Pink, Plate XXVI, pencilled with Thulite Pink, Plate XXVI. *Inner petal*—outside surface—Thulite Pink, Plate XXVI, with streak of white through center; inside surface—Cameo Pink, Plate XXVI, pencilled with Thulite Pink, Plate XXVI.

This description was made from a rose that was open for three days in a greenhouse, during August, 1942, at Richmond, Indiana:

*Color.—Outside petal*—outside surface—almost white at tip, shading to Cameo Pink, Plate XXVI; inside surface—almost white at tip, shading to Cameo Pink, Plate XXVI. *Inside petal*—outside surface—Cameo Pink, Plate XXVI; inside surface—Cameo Pink, Plate XXVI.

*General color effect.*—Newly opened flower—Rosalene Pink, Plate XXVI. Three days open—Cameo Pink, Plate XXVI.

*Behavior.*—Persist.

*Flower longevity.*—On bush in garden five days in July; cut flowers grown in greenhouse kept at living-room temperatures four to five days in March.

*Reproductive organs*

Stamens: Medium number; arranged irregularly abouts pistils.
Filaments: Short; White; most with anthers.
Anthers: Very small; Brown; all open at once.
Pollen: Moderate; Gold.
Pistils: Few.
Styles: Uneven; short; thin; bunched.
Stigma: White.
Ovaries: All enclosed in calyx.
Sepals: Permanent; moderately long; spear-shaped; curled.

*Color.—Inside*—Light Cress Green, Plate XXXI, overlaid with white fuzz. *Outside*—Light Cress Green, Plate XXXI.

*Plant*

Foliage:

*Leaves.*—Compound of five leaflets; very abundant; large; very heavy; leathery.

*Leaflets.*—Ovoid with apex acute; base round; margin simply serrate.

*Color.—Mature*—upper surface—very Dark Green; under surface—moderately Light Green. *Young*—upper surface—moderately Dark Green Bronze; under surface—moderately Light Green.

*Rachis.*—Heavy. Upper side—grooved; hairy. Under side—moderately smooth; hairy; prickly.

*Stipules.*—Moderately short; medium wide; with medium length points turning out at an angle of more than 45°.

*Disease.*—Resistant to mildew and blackspot.

Growth:

*Habit.*—Bush; upright; much branched.

*Growth.*—Vigorous.

*Canes.*—Medium heavy.

*Main stems.*—Green Brown. *Thorns*—several; medium length; hooked downward; with long narrow base. *Prickles*—several; Green-Bronze. *Hairs*—none.

*Branches.*—Bright Green. *Thorns*—several; medium length; hooked downward; with long narrow base. *Prickles*—several; Green-reddish. *Hairs*—none.

*New shoots.*—Bright Green Bronze Red. *Thorns*—several; medium length; hooked downward; with long narrow base. *Prickles*—several; Reddish. *Hairs—none.*

I claim:

A new and distinct variety of rose plant of the polyantha class, characterized as to novelty by its habit of vigorous growth with relatively large foliage; greater productivity of large flowers growing on long stems, having more numerous petals, especially adapting it to cut flower as well as garden decoration purposes, and novel coloring of the flowers, substantially as shown and described.

ROY L. BYRUM.